United States Patent [19]

Braginetz

[11] Patent Number: 4,666,435
[45] Date of Patent: May 19, 1987

[54] SHIELDED MEDICAL SYRINGE

[76] Inventor: Paul A. Braginetz, 214 Oak Ridge Cir., Staunton, Va. 24401

[21] Appl. No.: 865,870

[22] Filed: May 22, 1986

[51] Int. Cl.⁴ .............................................. A61M 5/32
[52] U.S. Cl. .................................................. 604/198
[58] Field of Search ................ 604/198, 197, 192, 263

[56] References Cited

U.S. PATENT DOCUMENTS 3,890,971  6/1975  Leeson et al. ........................ 604/198
4,573,976  3/1986  Sampson et al. ..................... 604/198

Primary Examiner—John D. Yasko
Attorney, Agent, or Firm—Brady, O'Boyle & Gates

[57] ABSTRACT

To protect patients, medical and hospital personnel against the spread of infectious diseases, a molded syringe vial is equipped on its exterior with an array of tracks, rails, stops and detents which can cooperate with elements on an external shield to enable the shield to be first held on the vial in a position allowing normal usage of the medical syringe for injecting or withdrawing fluids, and to be subsequently moved to a non-releasable locked position on the vial in which the contaminated needle of the syringe is completely covered. The shield is manipulated on the vial through a series of simple longitudinal and rotational movements. The syringe lends itself to current mass production economical molding techniques with no alteration of the vial piston bore or piston.

12 Claims, 25 Drawing Figures

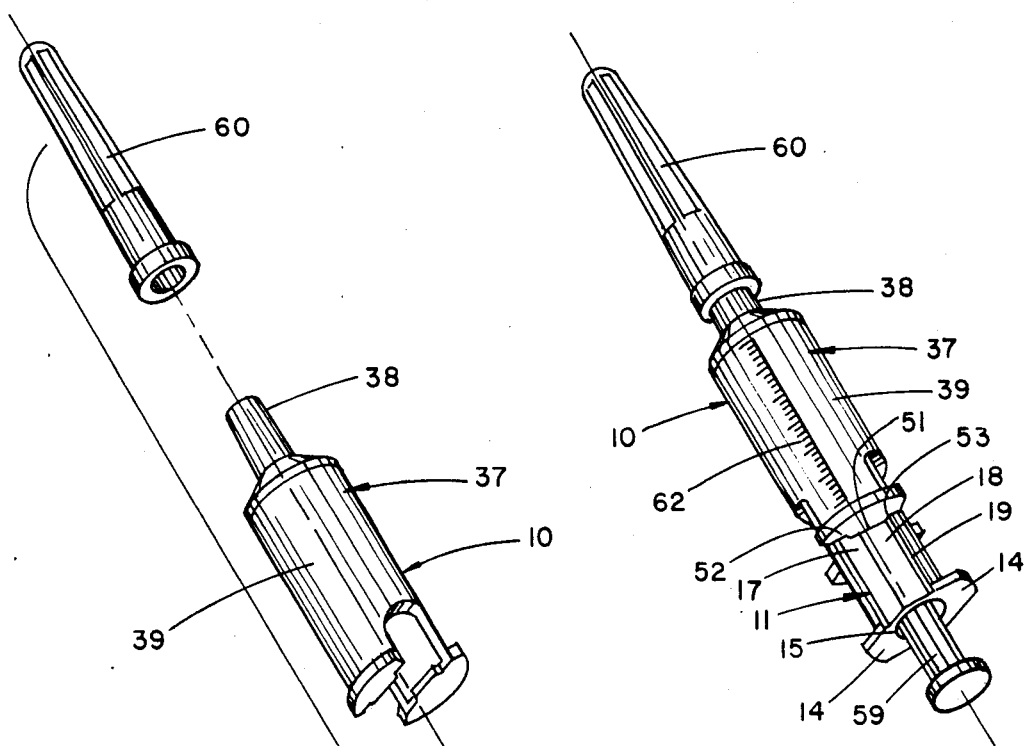
FIG. 1
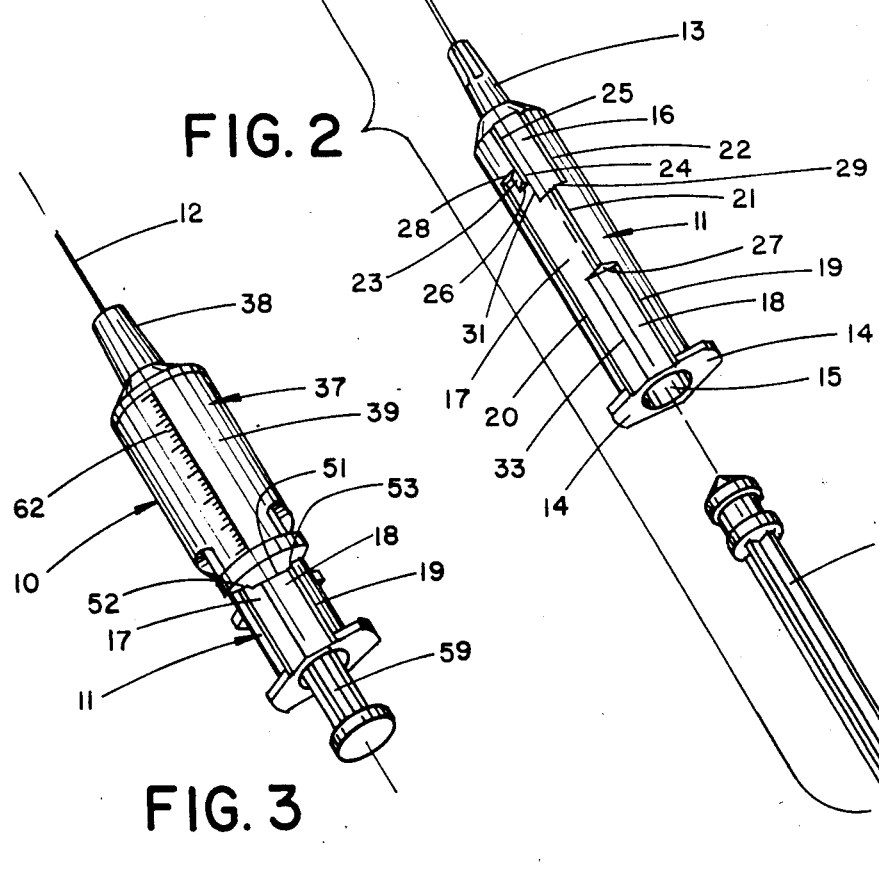
FIG. 2
FIG. 3

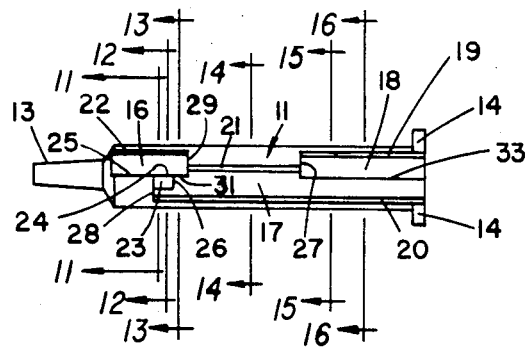
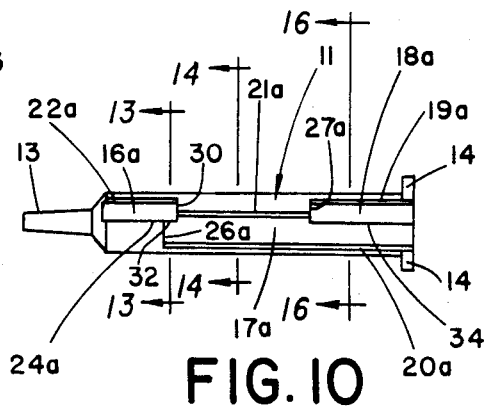
FIG. 9
FIG. 10
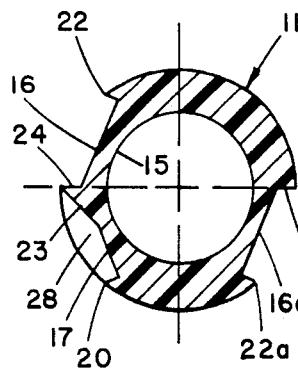 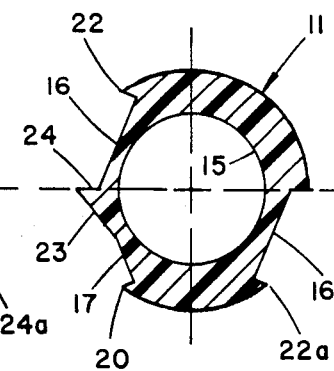 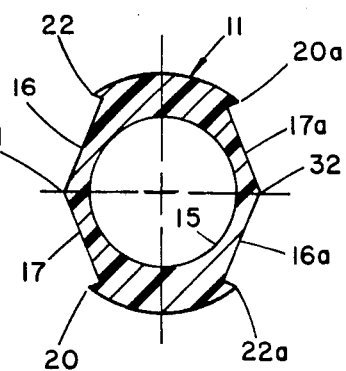
FIG. 11    FIG. 12    FIG. 13
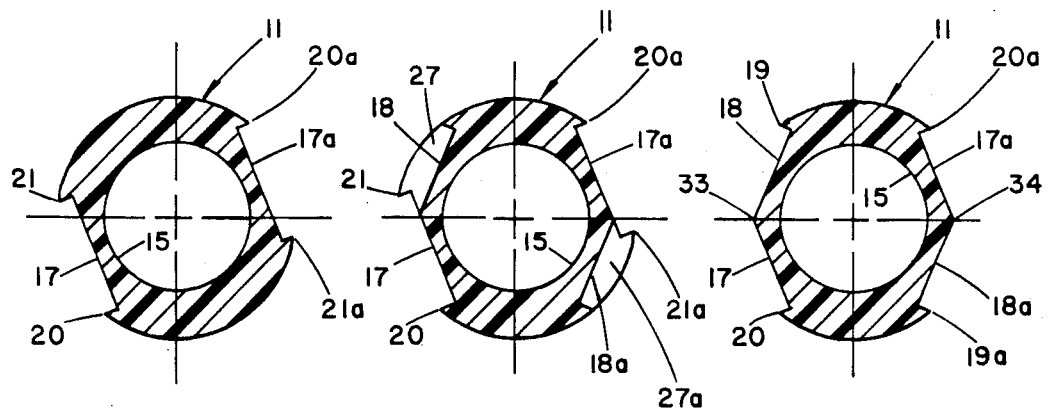
FIG. 14    FIG. 15    FIG. 16

SHIELDED MEDICAL SYRINGE

BACKGROUND OF THE INVENTION

1. Technical Field

The present invention relates to a medical syringe of the type in which the syringe needle is shielded to protect against the spread of infectious diseases, including AIDS and serum hepatitis.

2. Description of the Prior Art

U.S. Pat. No. 4,425,120, Sampson et al., discloses a shielded hypodermic syringe for the general purposes of the present invention. However, the syringe structure in the Sampson et al. patent does not lend itself to manufacturing by mass production molding techniques with maximum economy, partly due to the necessity of installing on the exterior of the syringe barrel or vial track-engaging rollers. Therefore, it is a prime objective of this invention to improve on the prior patented device by providing a disposable shielded syringe which lends itself to the most economical modern day molding processes to produce a geometric form on the exterior of the syringe barrel or vial, whereby the operation of the exterior shield on the syringe vial is rendered more convenient, more positive and safer in terms of locking the shield in its contaminated needle enclosing position on the vial.

SUMMARY OF THE INVENTION

The present invention is best summarized as a molded plastics disposable shielded medical syringe in which an exterior syringe shield is formed with elements which cooperate with external surface elements on the syringe vial to allow placing the shield in a locked retracted position enabling normal usage of the syringe, and later placing the shield in an extended non-releasably locked position on the vial for fully enclosing the contaminated syringe needle, all by a simple sequence of rotational and longitudinal movements of the external shield relative to the vial and needle without disturbing normal construction and cooperative functioning of the syringe plunger and the bore of the vial which receives the plunger.

Other objects and advantages of the invention will become apparent to those skilled in the art during the course of the following detailed description.

BRIEF DESCRIPTION OF THE DRAWINGS

FIG. 1 is an enlarged tri-metric view of a shielded medical syringe according to the present invention as the device would be received from a medical supplier.

FIG. 2 is an exploded tri-metric view of the syringe shown in FIG. 1.

FIG. 3 is a further tri-metric view of the syringe with a needle shielding scabbard removed to expose the needle for normal usage.

FIG. 9 is an actual size side elevation of the syringe vial showing its three track system, the rear and front forward stops, the ramp lock, and the track side rails, all on the exterior of the molded vial.

FIG. 10 is a similar view showing the diametrically opposite side of the vial with a three track system, rear and forward stops, and the track side rails on the exterior of the molded vial.

FIG. 11 is an enlarged transverse vertical section taken on line 11—11 of FIG. 9.

FIG. 12 is a similar section taken on line 12—12 of FIG. 9.

FIG. 13 is a similar section taken on line 13—13 of FIGS. 9 and 10.

FIG. 14 is a similar section taken on line 14—14 of FIGS. 9 and 10.

FIG. 15 is a similar section taken on line 15—15 of FIG. 9.

FIG. 16 is a similar section taken on line 16—16 of FIGS. 9 and 10.

DETAILED DESCRIPTION

Figure 4:
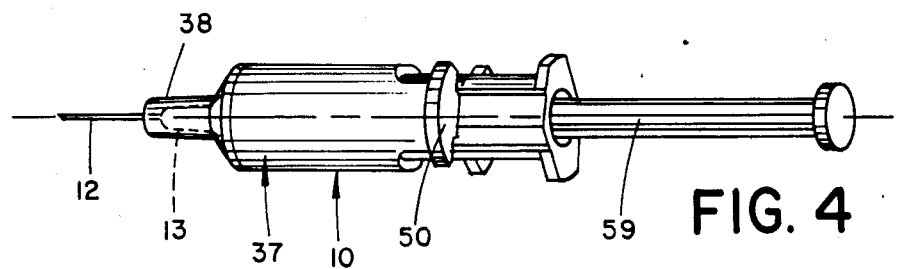
FIG. 4 is a similar view of the syringe with its piston retracted, indicating that the syringe is loaded with fluid.

Referring to the drawings in detail in which like numerals designate like parts, a medical syringe 10 according to the present invention includes a vial 11 to the forward end of which is permanently affixed a syringe needle 12. The needle 12 is mounted in a vial nozzle 13 by cold forming, as shown in FIG. 2. The rear end of the vial 11 is equipped with finger flanges 14 and the bore 15 or well of the vial is cylindrical and smooth in accordance with conventional practice.

In accordance with the essence of the invention, the exterior surface of the vial 11 is configured by molding techniques to provide thereon tracks 16, 17 and 18 and rails 19, 20, 21 and 22. A ramp 23 and lock surface 24, with the foregoing elements, are all on one side of the vial 11, as shown clearly in FIGS. 2 and 9.

FIG. 10 illustrates the diametrically opposite side of the vial 11 whose molded configuration differs from the side shown in FIG. 9 in that the ramp 23 and lock 24 are omitted. To form the lock surface 24, FIG. 9, it was necessary to continue the surface 24 at 25 in the tool design, for a proper steel shut-off. The extended surface 25 has no function in the product. Front stops 26 and 27 are also provided on the side of the vial 11 shown in FIGS. 2 and 9 having the lock 24.

Figure 8:
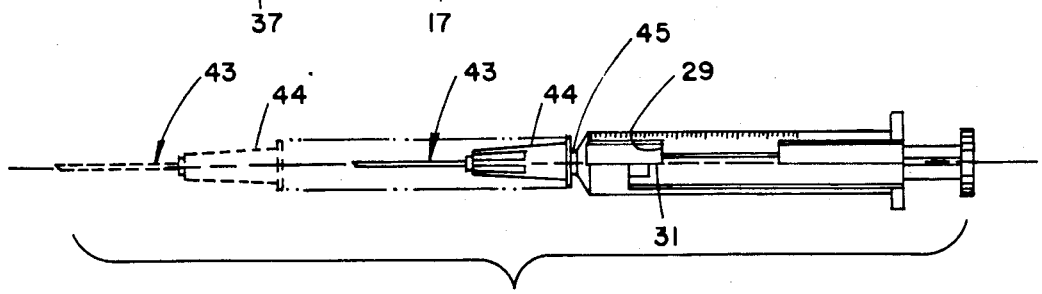
FIG. 8 is a side elevation in actual size of the syringe according to the invention showing another type of needle which can be assembled onto the nozzle of the syringe vial removably.

The front stop 26 is interrupted by the construction of ramp 23 and is continued as an offset stop surface 28. Additionally there are two rear stops 29 and 30 on the opposite sides of the vial 11, FIGS. 9 and 10. The rear stop 29 is also shown in FIGS. 2 and 8. A detent 31, FIGS. 2, 8 and 9, is formed at the chord intercept surfaces of tracks 16 and 17. Tracks 16a and 17a, FIG. 10, also form a detent 32. Tracks 17 and 18 likewise form a detent 33, FIG. 9, and tracks 17a and 18a, FIG. 10, form between them a detent 34.

Finger flanges 14 are 90° out of phase with the above-described vial surface construction. Without this arrangement, the vial could not be molded in a straight draw in the tool, and would necessitate forming the required geometry by side cam construction of the tool, which is expensive. The construction according to this invention can be produced within a die set of core and cavity construction having a simple draw opening.

The vial 11, as an option, may have imprinted on its surface a liquid scale 35 in accordance with the current state of the art. The scale 35 is located on the non-configured surface 36 of the vial 11, if used. The scale 35 would be red through a clear plastics shield 37, the details of which will be described. The imprinting of the scale 35 on the vial is a secondary operation following the molding step.

The shield 37 is a very important feature of the invention which protects careless and unsuspecting personnel while administering to infected patients against AIDS, serum hepatitis and the like.

Figure 17:
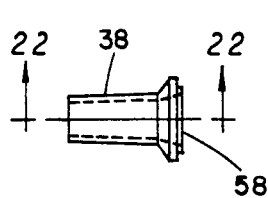
FIG. 17 is a side elevation of a nozzle front piece of the exterior shield as molded separately.
Figure 18:
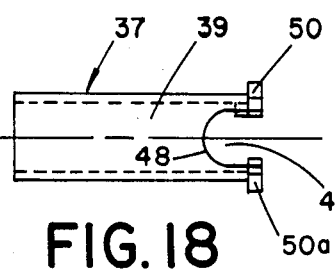
FIG. 18 is a similar view of the shield rear piece or body portion as molded separately showing stress riser relief notches.
Figure 20:
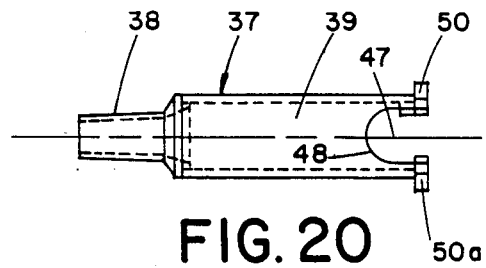
FIG. 20 is a side elevation of the assembled shield components in FIGS. 17 and 18 following ultrasonic fusing together thereof.

The shield 37 is manufactured as a unit from two components which are ultrasonically joined. A nozzle 38, FIG. 17, is formed separately from a sleeve body 39 of the shield 37, FIG. 18. These two components are seen ultrasonically joined as a unit in FIG. 20. The shield 37 is constructed to slip over and contain the syringe vial 11 which is ba2sically cylindrical except for its molded exterior geometry. The shield 37, therefore, is also cylindrical and sized to engage slidably on the cylindrical surface portion of the vial 11. Since the inside geometry of the sleeve body 39 cannot be molded integrally with the nozzle 38, the two components are formed separately and joined as described to form the shield 37.

Figure 21:
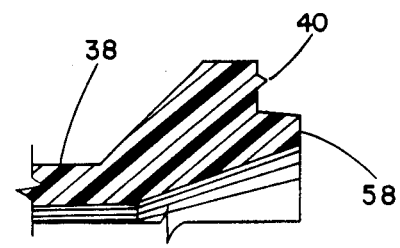
FIG. 21 is a greatly enlarged fragmentary vertical section of the abutting end of the nozzle front piece in FIG. 17.

FIG. 21 shows the ultrasonic bead 40 of the nozzle 38 which unifies the components 38 and 39. A plastics solvent can also be used to join the two components of the shield 37 but the ultrasonic method is preferred because of the hygienic cleanliness of the bead 40.

Figure 22:
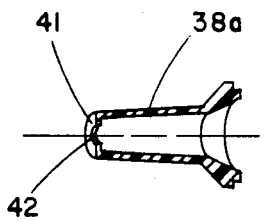
FIG. 22 is a vertical section in tri-metric projection taken on line 22—22 of FIG. 17 and showing a front wall partition having an aperture to accommodate the syringe needle therethrough.

A modified type of nozzle 38a for the shield 37 is shown in FIG. 22. This nozzle includes a front wall 41 having a needle orifice 42 formed therethrough to accommodate a demountable needle assembly 43 shown in FIG. 8. The needle of this assembly is affixed in a plastics cone 44 which is then fitted onto the vial nozzle 45 frictionally. This arrangement corresponds to the conventional state of the art. Should the needle assembly 43 become loose, it can be repositioned on the nozzle 45 by medical personnel. If the cone 44 were to be used with the shield 37, it could present problems because, when the shield 37 is in place, the demountable needle assembly 43 becomes inaccessible. Therefore, the use of the assembly 43 with the shield 37 is not recommended.

Figure 23:
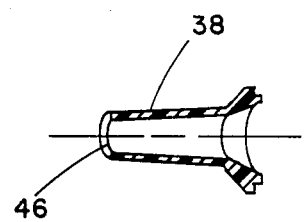
FIG. 23 is a similar tri-metric section of a shield nozzle without the front wall according to a variant of the invention.

Similarly, the nozzle 38 has an advantage over the nozzle 38a. When a needle passes through the orifice 42 of nozzle 38a, some contamination will be deposited on wall 41. Any arrangement which leaves contamination on a protected housing component is not the most recommended for the present invention. Therefore, the permanently fixed needle 12, FIG. 2, is ideal because the needle cannot be accidentally displaced during handling or shipping of the product. It further enhances the safeguards provided by the preferred nozzle 38 on which the needle orifice 42 is omitted along with the end wall 41. A larger nozzle opening 46 is provided as shown in FIG. 23.

Figure 24:
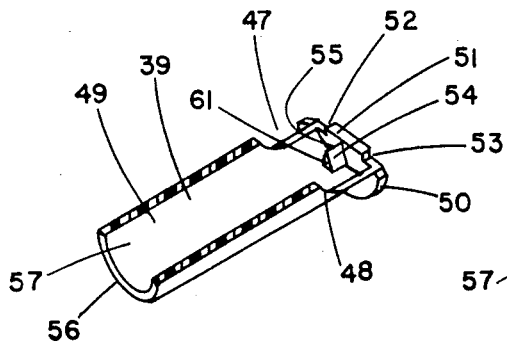
FIG. 24 is an enlarged tri-metric sectional view of the shield body portion taken on line 24—24 of FIG. 19.

The sleeve body 39, FIGS. 18, 19, 24 and 25, is provided with opposite side openings 47 having arcuate end walls 48. This construction forms a stress riser relief for the sleeve body portion 39. FIG. 24 depicts the lock half 49 of the sleeve component and shows a finger flange 50, partition chord 51 and rail notches 52 and 53. Thers is also a lock ramp 54 on the lock half 49 of the sleeve body portion 39 and a lock surface 55, FIG. 24. Circumferential edge 56, FIG. 24, is used to unite with the matching circumferential face of nozzle 38. The inside surface 57 of component 49 concentrically positions the sleeve body portion 39 accurately in abutment with the nozzle 38 during the sonic assembly process by receiving the end projection 58 of the nozzle 38, FIG. 21. FIG. 24 shows the sleeve body 39 as viewed along section line 24—24 of FIG. 19.

Figure 19:
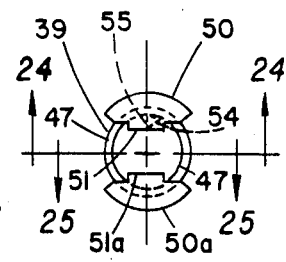
FIG. 19 is an end elevation of the sleeve body portion shown in FIG. 18 showing details of track registration chord partitions used as rear and front displacement stops, counter-rotational lock, track side notches and stress riser relief flanges.
Figure 25:
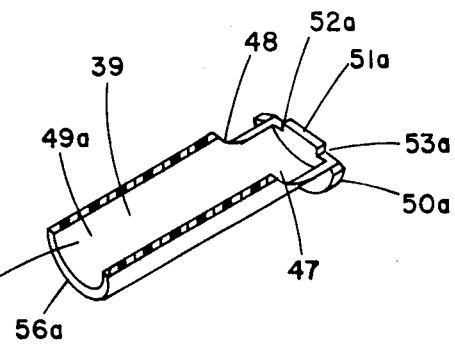
FIG. 25 is a similar section taken on line 25—25 of FIG. 19.

FIG. 25 shows the sleeve body portion 39 as viewed along the section line 25—25 of FIG. 19. The ramp 54 and lock surface 55 are absent. In all other respects, the sleeve half component 49a, FIG. 25, is the same as the component 49 of FIG. 24 and includes a finger flange 50a, partition chord 51a, rail notches 52a and 53a, circumferential edge 56a and inside surface 57a.

The syringe further comprises a conventional piston 59 and a needle cover or scabbard 60, as shown in the drawings.

ASSEMBLY OF COMPONENTS

All components must be hygienically clean. To complete the assembly of the syringe 10, as shown in FIG. 1, refer to FIG. 2 of the drawings. The piston 59 is first inserted into the bore 15 of vial 11. The outside diameter of the vial is slightly smaller than the inside diameter of shield 37. Partition chords 51 and 51a are parallel and the distance between their edges is somewhat smaller than the outside diameter of the vial 11. The vial nozzle 13 is inserted into the rear opening of the shield 37. The parallel edges of partition chords 51 and 51a are aligned with tracks 17 and 17a of the vial 11. The parallel edges will spread apart to the limit of the outside diameter of vial 11 due to the resiliency of the plastics material. When the front stops 26 and 26a, FIGS. 9 and 10, are passed, the partition chords will snap onto tracks 17 and 17a. The rail notches 52 and 53 will align with rails 20 and 21 on track 17, and the rail hotches 52a and 53a will nest with rails 20a and 21a of track 17a FIG. 10. In this engagement with the vial 11, shield 37 can move along tracks 17 and 17a and is prevented from rotating by the partition chords 51 and 51a and is enforced by side rails 21 and 21a. The vial 11 is pushed forwardly in the shield 37 until the nozzles 13 and 38 are fully nested, at which point the insertion of the vial into the shield is completed.

It is now possible to rotate the shield 37 clockwise on the vial 11, and the shield is rotated clockwise onto tracks 18 and 18a. In so doing, the chords 51 and 51a will override detent 33, FIGS. 2 and 9, and detent 34, FIG. 10. These detents resist rotation of the shield 37 and prevent it from being accidentally rotated while oriented with a particular set of tracks on the vial. At the location of full insertion, just beyond front stops 27 and 27a, the shield 37 can be rotated but not otherwise. It should be noted that the stops 27 and 27a are located in different circumferential planes on the vial 11, FIGS. 9 and 10. As measured from the finger flanges 14, track 18 is longer than track 18a to accommodate the width of the ramp 54 shown in FIG. 24.

Therefore, the ramp front face 61, FIG. 24, prevents the shield 37 from moving forwardly against front stop 27 on track 18 while the inside surface of partition chord 51a prevents the shield from moving forwardly against the front stop 27a on track 18a, FIG. 10.

Finally, the scabbard 60 is placed on the tapered nozzle 38 removably with a friction fit. In the prior art pertaining to medical syringes, the needle is normally protected by the sheath which mounts on the syringe barrel or vial directly. In contrast to this, in the present invention, the scabbard 60 or sheath mounts on the shield 37 rather than on the vial and this concept is unique. The syringe in its completely assembled state shown in FIG. 1 is ready for use by medical personnel.

OPERATION

The user of the syringe, as shown in FIG. 1, will first remove the scabbard 60 from the shield 37 and the scabbard can be discarded. Its only use is to protect the needle 12 from contamination in transit and in handling prior to use. After removal of the scabbard 60, the syringe 10 will appear as shown in FIG. 3. The shield 37 is fully engaged with the vial 11 and partition chord 51 is registered to track 18. Rail notch 53 is in engagement with outside rail 19 bordering track 18. Rail notch 52 is not engaged with a rail and simply overlies track 17.

The syringe needle 12 can now draw blood from a patient or draw medication from a bottle. The volume of extracted fluid can be accurately measured on a scale 62, FIG. 3, which can be provided on the shield 37, as opposed to a similar scale on the vial 11 in accordance with conventional practice. The scale 62 on the shield 37 may be preferable in this invention since the shield overlies the vial 11. Also, the vial liquid scale 35 shown in FIG. 6 may sustain abrasion when the shield 37 is placed on the vial resulting in a scrap rate detrimental to manufacture. On the other hand, the liquid scale 62 could be misread due to refraction and this would indicate a preference for placing the scale on the vial 11 to be read through the clear plastics shield 37. Either scale arrangement could be employed, as found desirable.

Figure 5:
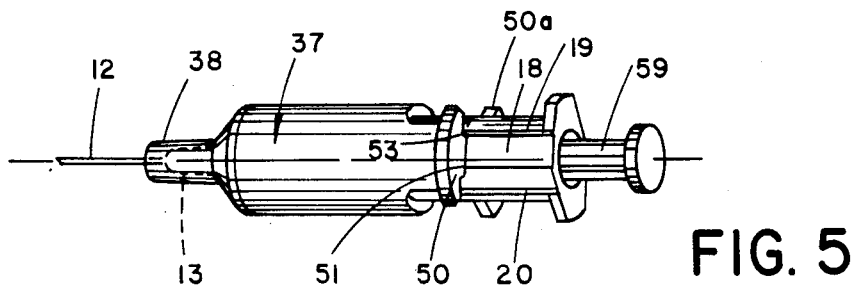
FIG. 5 is a similar view showing the piston pushed forwardly, indicating that the fluid has been discharged and the needle is contaminated.

FIG. 4 shows the syringe 10 with the piston 59 fully retracted indicating that the syringe vial contains fluid. FIG. 5 shows the piston 59 thrust forwardly to the fluid unloading position. The needle 12 and the entire device may now be contaminated. Thus far, the shield 37 has no function and, up to this point, the syringe has been used in a conventional manner.

Figure 6:
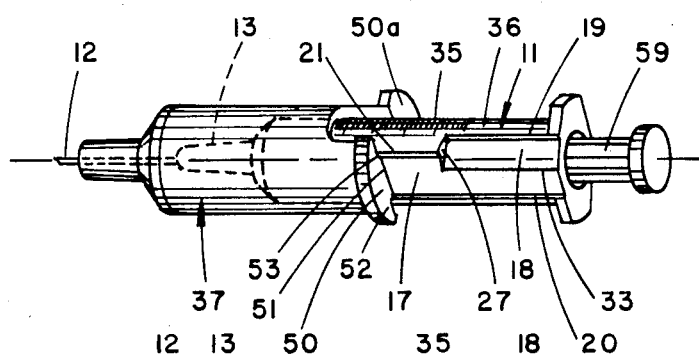
FIG. 6 is a similar view of the syringe following counterclockwise rotation and partial advancement of the shield on the syringe vial to a position where the shield partially covers the contaminated needle.

FIG. 6 depicts the first functioning of the shield 37. Finger flanges 50 and 50a are rotated counterclockwise from track 18, as shown in FIG. 5, onto track 17, FIG. 6, and in circumferential plane maintaining the flanges 50 and 50a in place until the surface 61, FIG. 24, and inside partition chord 51a, FIG. 25, clear the forward stop 27, FIGS. 2 and 9, and the forward stop 27a, FIG. 10. Rail notch 53 is disengaged from outside rail 19 in the relationship of rotation shown in FIG. 6. Rail notch 52 engages outside rail 20 to prevent override of track 17, FIG. 6. Of course, under the force of physical rotation, the detents 33 and 34 were overridden by the partition chords 51 and 51a.

The shield 37 can now be moved forwardly on the vial 11. As this is done in the interim position shown in FIG. 6, it is seen that rail notch 53 has picked up outside rail 21 on vial 11, and rail notch 53a has picked up outside rail 21a on the vial 11, FIG. 10. In this position of transfer shown in FIG. 6, the shield 37 cannot be rotated on the vial and can only be displaced along the axis of the vial 11.

From the interim position of FIG. 6, the shield 37 is moved forwardly until surface 61, FIG. 24, strikes surface 28, FIG. 2, and the inside surface of partition chord 51 strikes front stop surface 26. These four surfaces as paired come into contact simultaneously as stops for the shield 37 on the lock half 49 of sleeve body portion 39. Diametrically opposite, when the shield 37 is brought forward, the inside surface of partition chord 51a strikes the surface of front stop 26a on the sleeve half component 49a of sleeve body portion 39.

Figure 7:
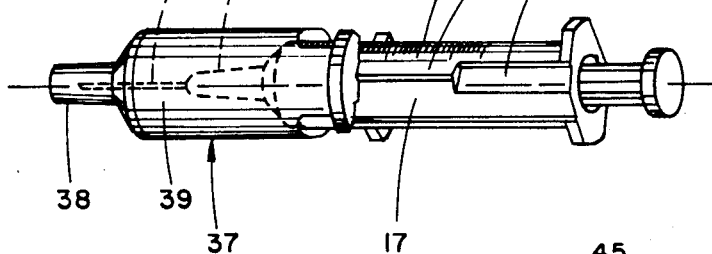
FIG. 7 is a similar view showing the shield fully advanced against front forward stops of the syringe vial, the syringe having been rotated clockwise from its position in FIG. 6 by way of overriding detents and the ramp lock on the vial, the shield now being non-releasably locked in the needle enclosing position.

In this forward position, the shield 37 can be rotated clockwise from track 17 to track 16, as shown in FIG. 7. The following takes place simultaneously:

(a) Ramp 54 on the inside of the shield 37, FIG. 4, rides up ramp 23 on the vial 11, FIG. 2.

(b) The detent 31, FIGS. 2 and 9, is not touched by partition chord 51 because the chord is raised by the ramp.

(c) The detent 32, FIG. 10, is overridden by the partition chord 51a, and this partition is sandwiched between front stop surface 26a and rear stop surface 30, FIG. 10. While the ramp 23 elevates ramp 54, only partition chord 51a holds the shield 37 against moving forwardly or rearwardly.

(d) When ramp 54 overrides ramp 23, the side openings 47 on sleeve body portion 39 are spread. This spreading is allowed without fracturing the sleeve element because of the arcuate end walls 48, FIG. 18, which relieve stresses.

(e) In FIG. 24, lock surface 55 on the sleeve body portion 39, FIG. 19, drops off of ramp 23 on vial 11 and the lock surface 55 is then located behind lock surface 24 on the vial 11. These two surfaces 55 and 24 lie in radial planes to the centers of the component parts, and therefore are face-to-face with each other. This is an effective lock which prevents counterclockwise rotation of the shield 37.

(f) The rail notches 52 and 52a were disengaged from outside rails 20 and 20a when the clockwise rotation started.

(g) The rail notches 53 and 53a engage outside rails 22 and 22a when the clockwise rotation was completed. These notches and rails act to prevent rotational override of the shield 37 on the vial 11.

It may now be seen that the shield 37 is locked in the position shown in FIG. 7, and cannot be rotated in either direction, nor can it be displaced forwardly or rearwardly. When partition chords 51 and 51a are registered to tracks 16 and 16a, respectively, forward lock surfaces and rear lock surfaces are in position on both sides of the shield partition surfaces. As seen in FIG. 7, the needle 12 is fully recessed in the nozzle 38 of the shield 37 and is also within the sleeve body portion 39 of the shield. The permanently locked syringe assembly can now be safely handled by medical or hospital personnel without the possibility of accidental needle puncturing and infection with AIDS, hepatitis or other diseases. The final disposal of the syringe is accomplished by incineration.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A medical syringe comprising a syringe vial having an attached needle and a piston bore, a piston operatively engaged in said bore, a shield rotationally and longitudinally movably engaged on said vial, cooperative means on said shield and vial to releasably hold said shield in a retracted position on the vial allowing normal usage of the syringe and to permanently lock the shield in a forward needle-enclosing position on the vial following normal usage of the syringe, said cooperative means on the vial being formed entirely by molding the exterior of the vial to produce an arrangement of tracks, rails, detents and stop surfaces thereon, said shield including a sleeve body portion having telescoping engagement with the exterior of the vial and being divided at its rear end, the divided rear end parts of the sleeve body portion including a pair of spaced parallel edge partition chords adapted to engage the tracks of the vial and to yieldingly engage detents of the vial, and the sleeve body portion having rail notches adjacent to said partition chords adapted to engage and follow rails of the vial.

2. A medical syringe as defined in claim 1, and the vial having a volumetric liquid scale visibly marked thereon, and the sleeve body portion of the shield being transparent to enable reading of the volumetric liquid scale on the vial therethrough.

3. A medical syringe comprising a syringe vial having an attached needle and a piston bore, a piston operatively engaged in said bore, a shield rotationally and longitudinally movably engaged on said vial, cooperative means on said shield and vial to releasably hold said shield in a retracted position on the vial allowing normal usage of the syringe and to permanently lock the shield in a forward needle-enclosing position on the vial following normal usage of the syringe, said cooperative means on the vial being formed entirely by nolding the exterior of the vial to produce an arrangement of tracks, rails, detents and stop surfaces thereon, said tracks rolded on the exterior of the vial including pairs of forward and rear tracks defining flat surfaces on diametrically opposite sides of the vial and another pair of tracks on the vial at diametrically opposed locations thereon defining flat surfaces, and the tracks of the last-named pair being circumferentially spaced on the vial from the tracks of the first-named pairs.

4. A medical syringe as defined in claim 3, and said rails of the vial extending longitudinally of the vial along longitudinal margins of the tracks of the vial, and said detents of the vial being defined on the exterior of the vial as longitudinal ridges at lines of intersection of planes occupied by adjacent pairs of said tracks.

5. A medical syringe as defined in claim 4, and said stop surfaces on the vial comprising radial stop surfaces located at corresponding interior ends of the forward and rear pairs of tracks.

6. A medical syringe as defined in claim 5, and another pair of radial stop surfaces on said vial on diametrically opposite sides thereof at corresponding ends of said another pair of tracks on the vial.

7. A medical syringe as defined in claim 6, and a ramp element on the vial at one side only of the vial adjacent to one of the last-named stop surfaces and defining another radial stop surface which is offset on the vial somewhat longitudinally rearwardly from the last-named stop surface.

8. A medical syringe as defined in claim 7, and a lock ramp element including a substantially radial lock surface within the rear end portion of said shield and being adapted during relative rotation of the shield and vial to engage and ride on said ramp element on the vial.

9. A medical disposable syringe adapted to be formed substantially from a moldable plastics material comprising a vial having an attached needle at its forward end and having a piston bore opening through its rear end, a piston operatively engaged in said piston bore, a shield engaged movably on the exterior of said vial and adapted in a fully retracted releasably locked position on the vial to expose the needle of the vial whereby the syringe can be used in a normal manner and adapted when in a forwardly advanced permanently locked position on the vial to substantially fully enclose said needle, means molded entirely on the exterior of the vial and cooperative means on the shield to releasably lock the shield in said fully retracted position, to permanently lock the shield in said forwardly advanced position and to allow controlled relative rotational and longitudinal movements of the shield and vial between said positions, said means molded entirely on the exterior of the vial comprising a first diameterically opposed pair of flat surface tracks on the vial extending forwardly from the rear end of the vial, a second pair of diametrically opposed flat surface tracks on the vial extending forwardly from the rear end of the vial to a point longitudinally forwardly of the first pair of tracks, the second pair of tracks being circumferentially spaced on the vial from the first pair of tracks, a third pair of flat surface diametrically opposed tracks on the vial longitudinally aligned with the first pair of tracks and extending through the forward end of the vial and being somewhat overlapped longitudinally at their rear end portions with forward end portions of the second pair of tracks, longitudinal detent ridges on the vial between the first and second pairs of tracks at the rear of the vial on diametrically opposite sides thereof, additional longitudinal detent ridges on the vial between the second and third pairs of tracks on diametrically opposite sides of the vial and being longitudinally aligned with the first-named detent ridges, longitudinal rails on the vial at diametrically opposite sides thereof between the forward ends of the first pair of tracks and the rear ends of the third pair of tracks, additional longitudinal rails on the vial along corresponding sides of the first, second and third pairs of tracks, a pair of front longitudinally spaced radial stop surfaces on the vial on diametrically opposite sides thereof, a pair of rear longitudinally spaced radial stop surfaces on the vial on diametrically opposite sides thereof, a ramp element defining a radial lock surface on the vial on one side thereof adjacent to one side of one track of the third pair of tracks and being located on one track of the second pair at the forward end thereof, a longitudinally offset radial stop surface on the vial on one side thereof at the forward end of said ramp and the forward end of the adjacent track of said second pair, said cooperative means on the shield comprising a pair of laterally spaced transverse parallel edge partition chords on the rear end of the shield adapted to selectively engage the tracks of the first, second and third pairs and to ride over said detents during rotation of the shield and to engage said radial stop surfaces of the vial, said shield having laterally spaced pairs of notches formed therein at the opposite sides of said partition chords and being adapted to selectively engage said rails of the vial in rotated positions of the shield on the vial, and a lock ramp having a radial lock surface on the shield at the forward side of one partition chord and adapted to engage and ride over said ramp element on the vial during rotation of the shield relative to the vial.

10. A medical syringe comprising a syringe vial having an attached needle and a piston bore, a piston operatively engaged in the piston bore, a shield rotationally and longitudinally movably engaged on the vial, cooperative means on the shield and vial operable in response to a predetermined sequence of relative rotational and longitudinal movements of the shield and vial to releasably hold the shield in a retracted position on the vial allowing normal usage of the syringe and to permanently lock the shield in a forward needle-enclosing position on the vial following normal usage of the syringe, and said cooperative means on the vial being formed entirely on the exterior of the vial.

11. A medical syringe as defined in claim 10, and the cooperative means on the vial including an arrangement of diametrically opposed tracks near opposite end portions of the vial, an arrangement of longitudinal guide rails along said tracks, a further arrangement of tracks partly coextensive longitudinally with the first-named arrangement of tracks, a further arrangement of longitudinal guide rails along the second-named arrangement of tracks and between the first-name arrangement of tracks on an intermediate portion of the vial, an arrangement of longitudinal and rotational stop surfaces and rotational detents, and the cooperative means on said shield including a divided end portion of the shield having parts adapted to engage with said tracks, guide rails, stop surfaces and detents during said relative rotational and longitudinal movements of the shield and vial.

12. A disposable medical syringe formed substantially from molded plastics components comprising a vial having an attached needle at its forward end and having a piston bore opening through its rear end, a piston operatively engaged in said piston bore, a sleeve-like shield engaged movably on the exterior of said vial, cooperative means on the shield and vial operable in response to a predetermined sequence of relative rotational and longitudinal movements of the shield and vial to releasably secure the shield in a retracted position on the vial and to permanently lock the shield in a forward needle-enclosing position on the vial, and the cooperative means on the vial being formed on the exterior of the vial by molding, the cooperative means on the shield including a pair of somewhat yielding spaced opposed rear extensions on the shield.

* * * * *